United States Patent
Martinez et al.

(10) Patent No.: US 11,744,642 B2
(45) Date of Patent: *Sep. 5, 2023

(54) ABLATION CATHETER WITH DUAL OPTICAL-ELECTRICAL STIMULATION AND SENSING

(71) Applicant: Medtronic, Inc., Minneapolis, MN (US)

(72) Inventors: Gonzalo Martinez, Mendota Heights, MN (US); Timothy G. Laske, Shoreview, MN (US); Mark T. Stewart, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 390 days.

This patent is subject to a terminal disclaimer.

(21) Appl. No.: 17/163,787

(22) Filed: Feb. 1, 2021

(65) Prior Publication Data
US 2021/0145515 A1    May 20, 2021

Related U.S. Application Data

(63) Continuation of application No. 15/786,229, filed on Oct. 17, 2017, now Pat. No. 10,939,959.

(51) Int. Cl.
*A61B 18/12* (2006.01)
*A61B 18/24* (2006.01)
(Continued)

(52) U.S. Cl.
CPC .......... *A61B 18/24* (2013.01); *A61B 18/1492* (2013.01); *A61B 90/30* (2016.02);
(Continued)

(58) Field of Classification Search
CPC ................ A61B 18/1492; A61B 18/24; A61B 2018/00059; A61B 2018/00577;
(Continued)

(56) References Cited

U.S. PATENT DOCUMENTS

| 5,722,403 A | 3/1998 | McGee et al. |
| 5,848,969 A | 12/1998 | Panescu et al. |

(Continued)

FOREIGN PATENT DOCUMENTS

| CN | 101332120 A | 12/2008 |
| CN | 103860142 A | 6/2014 |

(Continued)

OTHER PUBLICATIONS

China National Intellectual Property Administration Notice on the First Office Action for Application No. 201880067985.6 dated Jan. 20, 2023 (17 pages including English translation).

(Continued)

*Primary Examiner* — Daniel W Fowler
(74) *Attorney, Agent, or Firm* — Michael Best & Friedrich LLP (57) ABSTRACT

A device, system, and method for optically evaluating and treating or ablating tissue. Specifically, device, system, and method allow for the optical and/or electrical evaluation of tissue at the same location(s) at which ablation or treatment or ablation energy is delivered. This allows for a more accurate evaluation of lesion formation and tissue condition before, during, and/or after a treatment or ablation procedure. In one embodiment, a device for performing a medical procedure includes an elongate body including a proximal portion, a distal portion having a distal end, and a longitudinal axis, and a distal tip electrode at the elongate body distal end, the tip electrode being optically transparent and electrically conductive. The device may also include optical windows in the elongate body aligned with one or more transparent lateral electrodes for optically interrogating tissue and/or for delivering treatment or ablation energy to tissue.

20 Claims, 8 Drawing Sheets

(51) Int. Cl.
*A61B 18/14* (2006.01)
*A61B 90/30* (2016.01)
A61B 18/00 (2006.01)
A61B 90/00 (2016.01)
A61B 18/16 (2006.01)
A61B 1/00 (2006.01)

(52) U.S. Cl.
CPC . *A61B 1/00087* (2013.01); *A61B 2018/00059* (2013.01); *A61B 2018/00577* (2013.01); *A61B 2018/00791* (2013.01); *A61B 2018/00839* (2013.01); *A61B 2018/00982* (2013.01); *A61B 2018/162* (2013.01); *A61B 2090/306* (2016.02); *A61B 2090/373* (2016.02); *A61B 2218/002* (2013.01)

(58) Field of Classification Search
CPC .......... A61B 2018/00791; A61B 2018/00839; A61B 2018/00892; A61B 2018/162
See application file for complete search history.

(56) References Cited

U.S. PATENT DOCUMENTS

| | | |
|---|---|---|
| 5,989,245 A | 11/1999 | Prescott |
| 5,991,650 A | 11/1999 | Swanson et al. |
| 6,658,279 B2 | 12/2003 | Swanson et al. |
| 7,527,625 B2 | 5/2009 | Knight et al. |
| 8,513,531 B2 | 8/2013 | Trigwell et al. |
| 2005/0113828 A1 | 5/2005 | Shields et al. |
| 2006/0030844 A1 | 2/2006 | Knight et al. |
| 2009/0131931 A1 | 5/2009 | Lee et al. |
| 2011/0011629 A1 | 1/2011 | Trigwell et al. |
| 2011/0130818 A1 | 6/2011 | Chen |
| 2011/0160720 A1 | 6/2011 | Johnson |
| 2012/0265184 A1 | 10/2012 | Sliwa et al. |
| 2014/0052119 A1 | 2/2014 | Stewart et al. |
| 2014/0163550 A1 | 6/2014 | Besser et al. |
| 2014/0293399 A1 | 10/2014 | Kimura et al. |
| 2016/0353978 A1 | 12/2016 | Miller et al. |

FOREIGN PATENT DOCUMENTS

| | | |
|---|---|---|
| CN | 104688332 A | 6/2015 |
| WO | 2006017517 A2 | 2/2006 |
| WO | 2013123020 A1 | 8/2013 |
| WO | 2016196845 A1 | 12/2016 |

OTHER PUBLICATIONS

Duygu Kuzum, et al. Transparent, Flexible, Low Noise Graphene Electrodes for Simultaneous Electrophysiology and Neuroimaging, NIH Public Access, Published in final edited form as: Nat Commun.; 5:5259.doi:10.1038/ncomms6259, 24 pages, Apr. 20, 2015.
International Search Report and Written Opinion dated Jan. 2, 2019, for corresponding International Application No. PCT/US2018/054192; International Filing Date: Oct. 3, 2018 consisting of 11 pages.

ABLATION CATHETER WITH DUAL OPTICAL-ELECTRICAL STIMULATION AND SENSING

CROSS-REFERENCE TO RELATED APPLICATION

This application is a continuation of U.S. application Ser. No. 15/786,229, filed Oct. 17, 2017.

STATEMENT REGARDING FEDERALLY SPONSORED RESEARCH OR DEVELOPMENT n/a

TECHNICAL FIELD

The present invention relates to a device, system, and method for optically evaluating and ablating tissue.

BACKGROUND

Minimally-invasive medical devices and procedures are desirable for treating a variety of cardiovascular maladies, such as cardiac arrhythmias including atrial fibrillation, and other irregularities in the transmission of electrical impulses through the heart. One such example of a minimally invasive therapy involves the treatment of cardiac arrhythmias or irregular heartbeats in which physicians employ specialized cardiac assessment and treatment devices, such as mapping catheters and ablation catheters, to gain access to, diagnose, and treat interior regions of a patient's body. Such devices may include energized electrodes or other ablation assemblies to create lesions or other anatomical effects that disrupt or block electrical pathways through the targeted tissue.

In the treatment of cardiac arrhythmias, a specific area of cardiac tissue having aberrant electrically conductive pathways is typically initially identified for subsequent treatment. Additionally, the treated tissue may be analyzed to determine whether the tissue has been successfully ablated (i.e. that the aberrant electrical conductivity through the tissue has been destroyed). This localization or identification can include first using a medical device such as a mapping catheter to obtain a baseline electrophysiological map of electrical activity in selected tissue. Therefore, characterization of an area of tissue before, during, and/or after a treatment procedure is important for determining treatment efficacy. Currently known devices are based primarily on electrical signals for mapping, analysis, and/or delivering energy. However, such electrical signals are not selective enough to differentiate between local myocyte depolarizations and far-field depolarizations or to identify cardiac tissue conditions such as ischemia or other disease conditions. Accordingly, it is desirable to provide devices, systems, and methods for evaluating or analyzing tissue before, during, and/or after a treatment procedure that provides information about cardiac tissue conditions.

SUMMARY

The present invention advantageously provides a device, system, and method for optically evaluating and treating or ablating tissue. Specifically, device, system, and method allow for the optical and/or electrical evaluation of tissue at the same location(s) at which ablation or treatment or ablation energy is delivered. This allows for a more accurate evaluation of lesion formation and tissue condition before, during, and/or after a treatment or ablation procedure.

In one embodiment, a device for performing a medical procedure includes an elongate body including a proximal portion, a distal portion having a distal end, and a longitudinal axis, and a distal tip electrode at the elongate body distal end, the tip electrode being composed of an optically transparent material and having a continuous layer of an optically transparent and electrically conductive material.

In one aspect of the embodiment, the distal tip electrode is composed of an optically transparent first material and the continuous layer is composed of an optically transparent and electrically conductive second material, the second material being different than the first material.

In one aspect of the embodiment, the distal tip electrode is composed of at least one of a transparent polymer, ceramic, sapphire, synthetic sapphire, yttria, yttria-alumina garnet, zinc selenide, germanium, cadmium telluride, barium fluoride, caesium iodide, magnesium fluoride, thallium bromoiodide, zinc sulphide, calcium fluoride, quartz, diamond, ruby, synthetic ruby, crystal, glass, and fused silica.

In one aspect of the embodiment, the second material is at least one of graphene and conductive diamond.

In one aspect of the embodiment, the device further comprises at least one optical fiber within the elongate body, the at least one optical fiber being in optical communication with the distal tip electrode. In one aspect of the embodiment, the distal tip electrode includes a proximal face and a curved distal surface, the proximal face lying in a plane that is orthogonal to the elongate body longitudinal axis. In one aspect of the embodiment, the distal tip electrode includes an optical fiber channel having an opening, the optical fiber opening being on the distal tip electrode proximal face.

In one aspect of the embodiment, the optical fiber channel extends within the distal tip electrode from the distal tip electrode proximal face to a location that is a distance from the distal tip electrode curved distal surface.

In one aspect of the embodiment, the optical fiber channel is sized and configured to accept at least a portion of the at least one optical fiber.

In one aspect of the embodiment, the device further includes at least one optical window within the elongate body distal portion, the at least one optical window being composed of an optically transparent material.

In one aspect of the embodiment, the device further includes at least one lateral electrode on the elongate body distal portion, each of the at least one lateral electrode including at least one conductive area, each of the at least one conductive area being composed of an electrically conductive and optically transparent material.

In one aspect of the embodiment, the plurality of conductive areas are on a flexible overlay, the elongate body having an outer surface, the flexible overlay being applied to the elongate body outer surface. In one aspect of the embodiment, the flexible overlay is at least partially composed of an optically transparent material such that the plurality of conductive areas and flexible overlay are optically transparent, the flexible overlay being applied to the elongate body such that at least some of the plurality of conductive areas are positioned over at least one of the at least one optical window.

In one aspect of the embodiment, the at least one optical fiber is a first at least one optical fiber, the device further comprising a second at least one optical fiber, each of the second at least one optical fiber being in optical communication with one of the at least one optical window.

In one aspect of the embodiment, the at least one lateral electrode is a length of conductive material wound around at least a portion of the elongate body.

In one aspect of the embodiment, the distal tip electrode includes a plurality of apertures, the plurality of apertures configured to be in fluid communication with a fluid source.

In one embodiment, a system for evaluating and ablating an area of tissue includes: a medical device including: an elongate body including a proximal portion, a distal portion having a distal end, and a longitudinal axis; a distal tip electrode at the elongate body distal end, the distal tip electrode being optically transparent and electrically conductive; a first plurality of optical fibers within the elongate body and in optical communication with the distal tip electrode; at least one optical window within the elongate body distal portion, the at least one optical window being composed of a transparent material; a second plurality of optical fibers within the elongate body and in optical communication with the at least one optical window; at least one lateral electrode on the elongate body distal portion, the at least one lateral electrode being a plurality of electrically conductive and optically transparent graphene areas, the plurality of electrically conductive and optically transparent graphene areas being aligned with the at least one optical window such that the plurality of electrically conductive and optically transparent graphene areas and the at least one optical window are configured to transmit light therethrough; and a control unit including: a light emitter in optical communication with each of the first plurality of optical fibers and the second plurality of optical fibers; a light receiver in optical communication with each of the first plurality of optical fibers and the second plurality of optical fibers; an ablation energy source in communication with the distal tip electrode and the at least one lateral electrode; and processing circuitry in communication with the first plurality of optical fibers, the second plurality of optical fibers, the distal tip electrode, and the at least one lateral electrode.

In one aspect of the embodiment, the system is configured to deliver treatment energy from the at least one lateral electrode to an area of tissue and to emit and receive light through the at least one lateral electrode and the at least one optical window to and from the same area of tissue.

In one aspect of the embodiment, the processing circuitry is configured to: emit light from the light emitter through at least one of the distal tip electrode and the at least one lateral electrode through at least one of the first plurality of optical fibers and the second plurality of optical fibers to the area of tissue; receive light fluoresced from the area of tissue through at least one of the distal tip electrode and the at least one lateral electrode through at least one of the first plurality of optical fibers and the second plurality of optical fibers; and determine whether the area of tissue has been ablated based on the received light.

In one embodiment, a system for evaluating and ablating an area of tissue includes: an elongate body including a proximal portion, a distal portion having a distal end, and a longitudinal axis; a distal tip electrode at the elongate body distal end, the distal tip electrode being optically transparent and electrically conductive; a first plurality of optical fibers within the elongate body and in optical communication with the distal tip electrode; a plurality of optical windows within the elongate body distal portion, the at least one optical window being composed of an optically transparent material; a second plurality of optical fibers within the elongate body, each of the second plurality of optical fibers being in optical communication with at least one of the plurality of optical windows; a flexible overlay applied to at least a portion of the elongate body distal portion, the flexible overlay having: at least one layer composed of a flexible and optically transparent material; a plurality of electrically conductive and optically transparent graphene areas on the at least one layer, the plurality of graphene areas being aligned with at least one of the plurality of optical windows; and a conductive contact pad in electrical communication with the plurality of graphene areas; and a control unit including: a light emitter in optical communication with each of the first plurality of optical fibers and the second plurality of optical fibers; a light receiver in optical communication with each of the first plurality of optical fibers and the second plurality of optical fibers; an ablation energy source in communication with the distal tip electrode and the flexible overlay conductive contact pad; and processing circuitry in communication with the first plurality of optical fibers, the second plurality of optical fibers, the distal tip electrode, and the flexible overlay conductive contact pad, the processing circuitry being programmed to: deliver ablation energy to the area of tissue through at least one of the distal tip electrode and the plurality of graphene areas; emit light from the light emitter through at least one of the distal tip electrode and the at least one lateral electrode through at least one of the first plurality of optical fibers and the second plurality of optical fibers to the area of tissue; receive light that is at least one of fluoresced and reflected from the area of tissue through at least one of the distal tip electrode and the at least one lateral electrode through at least one of the first plurality of optical fibers and the second plurality of optical fibers; and determine whether the area of tissue has been ablated based on the received light.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

The devices, systems, and methods described herein may be used to not only treat or ablate tissue, but also to optically and electrically evaluate the tissue, such as evaluating lesion formation and identifying tissue structures. Before describing in detail exemplary embodiments, it is noted the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

As used herein, relational terms, such as "first," "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

Figure 1:
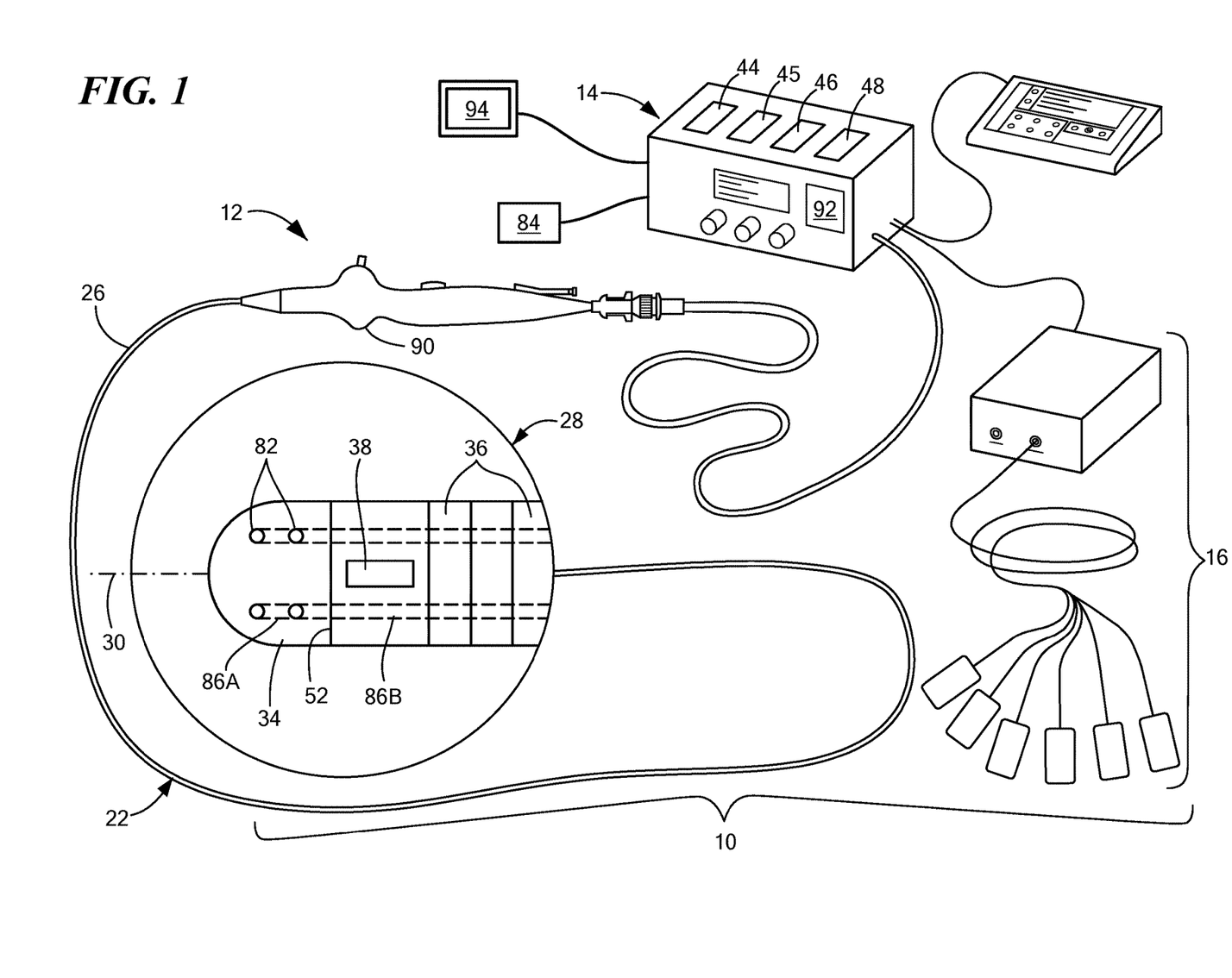
FIG. 1 shows an exemplary medical system.

Referring now to the drawing figures in which like reference designations refer to like elements, an embodiment of a medical system is shown in FIG. 1, generally designated as "10." The system 10 may generally include a treatment device 12 and a control unit 14. The system 10 may optionally include a navigation system 16, an imaging system such as near infrared (not shown) for obtaining images of anatomical features within a patient, and/or other system components for performing a particular medical procedure.

The treatment device 12 may be a treatment and mapping device. The device 12 may include an elongate body 22 passable through a patient's vasculature and/or proximate to a tissue region for diagnosis or treatment. For example, the device 12 may be a catheter that is deliverable to the tissue region via a sheath or intravascular introducer (not shown) or a device that can access the pericardial space. The elongate body 22 may define a proximal portion 26, a distal portion 28, and a longitudinal axis 30, and may further include one or more lumens disposed within the elongate body 22 thereby providing mechanical, electrical, and/or fluid communication between the elongate body proximal portion 26 and the elongate distal portion 28.

The device 12 may further include one or more treatment elements at, coupled to, or on the elongate body distal portion 28 for energetic, therapeutic, and/or investigatory interaction between the medical device 12 and a treatment site or region. The treatment element(s) may deliver, for example, radiofrequency energy, electroporation energy, laser energy, or other energetic transfer with a tissue area in proximity to the treatment element(s), including cardiac tissue, as discussed in more detail below. In some embodiments, the treatment element(s) may include an optically transparent and electrically and/or thermally conductive distal tip electrode 34 and, optionally, one or more electrically and/or thermally conductive electrodes 36 (which may be referred to herein as lateral electrodes 36) along a length of the elongate body distal portion 28 and/or one or more optically transparent optical windows 38 along a length of the elongate body distal portion 28. As used herein, the terms "transparent," "substantially transparent," and "optically transparent" refer to materials that are completely transparent as the term is understood in the art, or are at least sufficiently transparent to allow for optical imaging as discussed herein, even if the materials are not completely transparent. For example, the electrically and/or thermally conductive electrode(s) 36 and optical window(s) 38 may be located in or on the lateral wall of the catheter body 22, as opposed to the distalmost end of the elongate body 22. Further, the lateral electrode(s) 36 may be positioned over or aligned with the optical window(s) 38 to create a transparent area for optically or visually evaluating, energetically treating, and/or recording signals from tissue (thus, in some embodiments, the lateral electrode(s) 36 may be electrically and/or thermally conductive and optically transparent). The distal tip electrode 34 and, optionally, each of the optical windows 38 may be in optical communication with one or more optical fibers, a light emitter or source 44, and a light receiver 45. In one embodiment, the light emitter 44 is a laser emitter. Additionally or alternatively, the distal tip electrode 34 may be in communication with an energy source 46, such as a radiofrequency (RF) and/or high-voltage energy source, and, optionally, each of the optical windows 38 may be in communication with a laser energy source 48 for delivering laser energy to an area of tissue. Although not shown, the device 12 may include one or more additional types of treatment element, such as expandable elements (for example, balloons or baskets), ultrasound transducers, electrodes of other configurations than those shown, thermal treatment electrodes in communication with a cryogenic fluid source, or the like.

Figure 2:
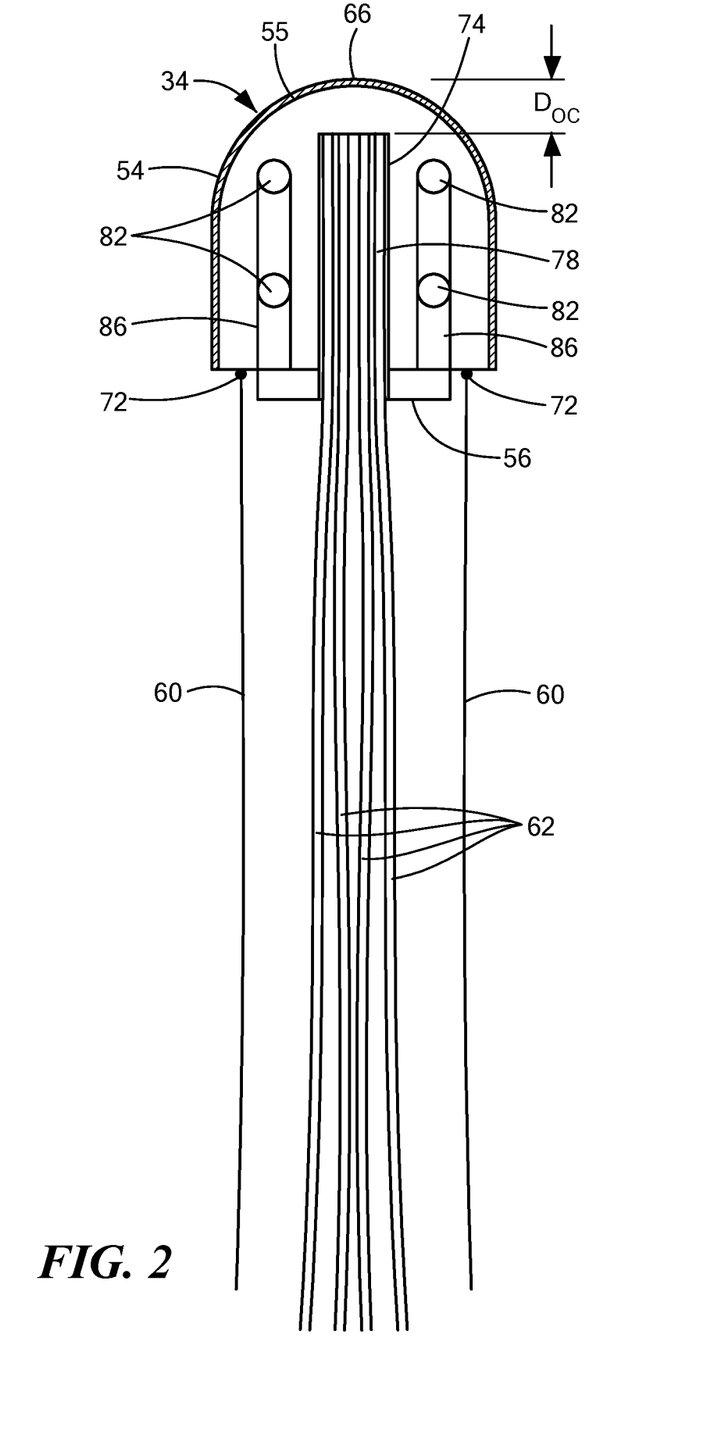
FIG. 2 shows a cross-sectional view of an exemplary optical distal tip electrode for use with the system of FIG. 1.
Figure 3:
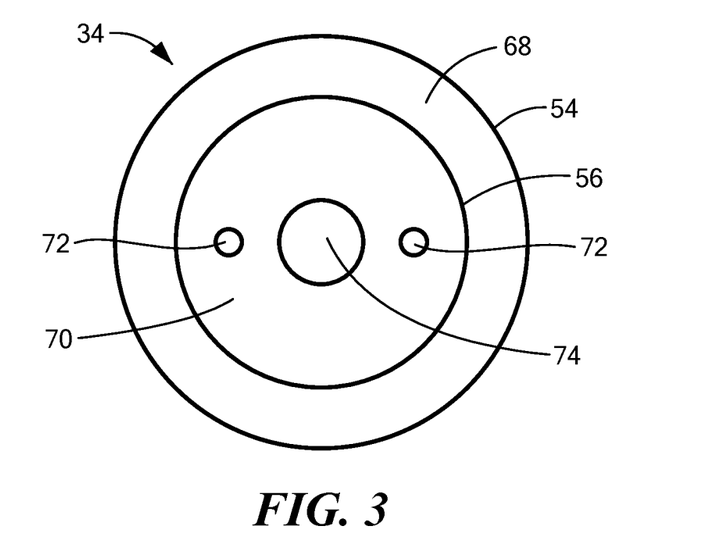
FIG. 3 shows a bottom view of a first configuration of the optical distal tip electrode of FIG. 2.
Figure 4:
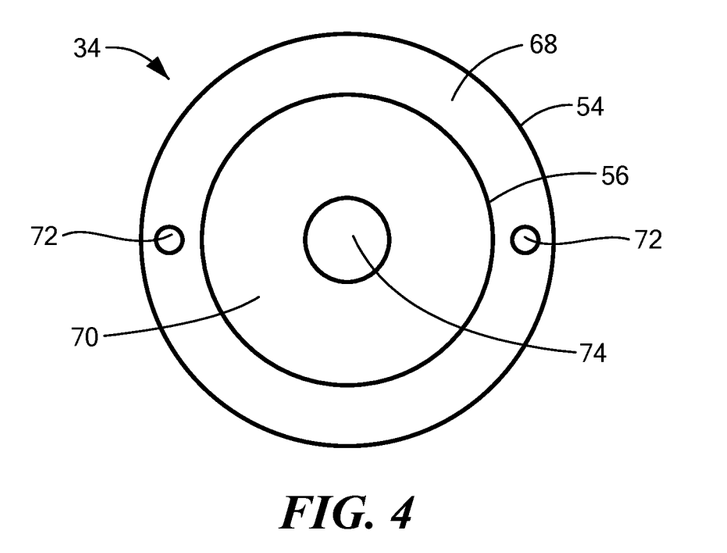
FIG. 4 shows a bottom view of a second configuration of the optical distal tip electrode of FIG. 2.

Referring to FIGS. 2-4, the distal tip electrode 34 of FIG. 1 is shown in more detail, unattached from the elongate body 22. In one embodiment, the distal tip electrode 34 is optically transparent and electrically and/or thermally conductive. For example, the distal tip electrode may be composed of one or more transparent materials such as transparent polymers, ceramics, sapphire, synthetic sapphire, yttria, yttria-alumina garnet, zinc selenide, germanium, cadmium telluride, barium fluoride, caesium iodide, magnesium fluoride, thallium bromoiodide, zinc sulphide, calcium fluoride, quartz, diamond, ruby, synthetic ruby, crystal, glass, fused silica, or the like. Further, to add electrical and/or thermal conductivity, at least a portion of the distal tip electrode 34 may be coated with or otherwise include a layer 55 of one or more transparent and electrically and/or thermally conductive materials such as graphene, conductive diamond, or the like. As a non-limiting example, a graphene film may be grown directly on a sapphire distal tip electrode 34 using chemical vapor deposition. Further, the layer 55 is a continuous layer that coats the entirety of, or at least substantially the entirety of, the portion of distal tip electrode 34 that is exposed from the elongate body 22 (as shown in FIG. 2), as opposed to being deposited, applied, or grown in a non-continuous pattern that leaves uncoated portions of the distal tip electrode 34. Thus, the continuous layer 55 may define the outer surface of the distal tip electrode 34. In one embodiment, the distal tip electrode 34 includes a head portion 54 and a neck portion 56, and the head portion 54 is coated with a layer of graphene or conductive diamond. In another embodiment, the distal tip electrode 34 does not include a neck portion. At least the distal tip electrode head portion 54, and optionally the distal tip electrode neck portion 56, may be composed of one or more transparent materials, and the distal tip electrode neck portion 56 may be composed of the same or different materials than the distal tip electrode head portion 54. Further, at least the distal tip electrode head portion 54 may include the layer 55 of transparent and electrically and/or thermally conductive material(s).

The distal tip electrode 34 may be configured to be coupled to the elongate body distal portion 28, for example, at a distal end 52 (a distalmost end face) of the elongate body distal portion 28. In one embodiment, the distal tip electrode neck portion 56 has an outer diameter that is sized to fit within a portion of the elongate body 22, such as within a central lumen or other space (for example, the outer diameter of the neck portion 56 is less than an inner diameter of an elongate body lumen). The distal tip electrode neck portion 56 and/or other area of the distal tip electrode 34 may be coupled or affixed to the elongate body 22, such as by chemical adhesives or bonding, thermal welding, friction fit, using one or more mechanical connecting elements, or the like. As is shown in FIG. 2, the distal tip electrode 34 may be configured to be coupled to one or more electrical wires 60 and to one or more optical fibers 62 (a plurality of optical fibers 62 may be referred to herein as a fiber optic bundle). Further, the distal tip electrode 34 may be configured to be coupled to the elongate body 22 such that the electrical wire(s) 60 and optical fiber(s) 62 may be located within the elongate body 22 when the device is assembled. In one embodiment, the distal tip electrode head portion 54 includes a distal surface 66 that may be curved and a proximal face 68 opposite the distal surface 66. The head portion proximal face 68 may have an outer diameter that is greater than the outer diameter of the distal tip electrode neck portion 56. The distal tip electrode neck portion 56 may also include a first end where the neck portion 56 joins the head portion 54 and a second end opposite the first end, the neck portion second end having a proximal face 70. The neck portion proximal face 70 may include one or more wire attachment elements 72, such as metalized rings or conductive pads (as shown in FIG. 3). Alternatively, one or more wire attachment elements 72 may be affixed to the head portion proximal face 68 where the proximal face 68 extends beyond the neck portion 56 (for example, as shown in FIG. 4). In either configuration, a distal portion of each of the one or more electrical wires 60 may be coupled to a corresponding wire attachment element 72, such that electrical signals from the distal tip electrode 34 may be received and transmitted through the electrical wire(s) 60 at the wire attachment elements 72. Further, each of the head portion proximal face 68 and the neck portion proximal face 70 may be planar or at least substantially planar and may each lie in a plane that is orthogonal or at least substantially orthogonal to the elongate body longitudinal axis 30. The curved distal surface 66 of the distal tip electrode 34 may have a convex shape that is curved away from the head portion proximal face 68. The portion of the distal tip electrode head portion 54 between the proximal face 68 and the distal surface 66 may have a cylindrical shape. However, it will be understood that the distal tip electrode 34 may have other shapes or configurations than those described herein. Although not shown, the elongate body 22 may include a conduit that extends from the elongate body distal portion 28 to the elongate body proximal portion 26 for each electrical wire 60. Alternatively, more than one electrical wire 60, and in some embodiments all of the electrical wires 60 (if the device includes a plurality of electrical wires 60), may be located within the same elongate body lumen. Thus, when the device 12 is assembled and the distal tip electrode 34 is coupled to the elongate body 22, the electrical wire(s) 60 may extend in a distal-to-proximal direction along the longitudinal axis 30 within the elongate body 22 toward the control unit 14.

In one embodiment, the distal tip electrode 34 further includes one or more optical fiber channels 74 that are sized to receive at least a portion of one or more optical fibers 62. In one embodiment, the distal tip electrode 34 includes one optical fiber channel 74 that extends at least within the head portion 54 of the distal tip electrode 34 from the head portion proximal face 68 to a location within the distal tip electrode head portion 54 that is a distance $D_{oc}$ from the head portion distal surface 66. In other words, each optical fiber channel 74 may be a blind channel with one opening, the opening being on the head portion proximal face. If the distal tip electrode 34 includes one optical fiber channel 74, the optical fiber channel 74 may have a longitudinal axis that is at least substantially coaxial with the elongate body longitudinal axis 30. If the distal tip electrode 34 includes a plurality of optical fiber channels 74, each optical fiber channel 74 may have a longitudinal axis that is at least substantially parallel to the elongate body longitudinal axis 30, and at least one optical fiber channel 74 may optionally have a longitudinal axis that is at least substantially coaxial with the elongate body longitudinal axis 30.

Further, in one embodiment, the distal tip electrode 34 may be manufactured such that the head portion 54 and neck portion 56 are integrated into a single piece composed of the same material. Alternatively, the distal tip electrode neck portion 56 may be composed of different material(s) than the material(s) from which the distal tip electrode head portion 54 is composed. In either of these configurations, the optical fiber channel 74 may extend from the neck portion proximal face 70, through the distal tip electrode neck portion 56, and through the distal tip electrode head portion 54 to the location within the distal tip electrode head portion 54 that is a distance Doc from the head portion distal surface 66, which the opening of the optical fiber channel 74 being located on the neck portion proximal face 70. As a further alternative, the distal tip electrode neck portion 56 may have a cylindrical configuration (not shown) that surrounds the opening of the optical fiber channel 74 located on the head portion proximal face 66.

The optical fiber channel 74 may have any cross-sectional shape, although a circular cross section is shown in FIGS. 3 and 4. Further, the optical fiber channel 74 may have an inner diameter that is sized to accept at least a portion of a distal portion 78 of at least one optical fiber 62. As a non-limiting example, the distal tip electrode 34 may include one optical fiber channel 74 that is sized to accept at least a portion of distal portions 78 of a plurality of optical fibers 62. In alternative non-limiting example, the distal tip electrode 34 may include a plurality of optical fiber channels 74, each of which being sized to accept at least a portion of a distal portion 78 of at least one optical fiber 62 (not shown). The optical fiber channel(s) 74 may be sized such that the optical fiber distal portions(s) 78 are held within the distal tip electrode 34 by a friction fit, or the optical fiber distal portion(s) 78 may be affixed within the optical fiber channel(s) 74, such as potted in position by adhesives. When the device 12 is assembled and the distal tip electrode 34 is coupled to the elongate body 22, the optical fiber(s) 62 may extend within the elongate body 22 in a distal-to-proximal direction along the longitudinal axis 30 from the distal tip electrode 34 toward the control unit 14.

The distal tip electrode 34 may optionally include one or more irrigation apertures 82 within the distal tip electrode head portion 54, and each irrigation aperture 82 may be in fluid communication with a fluid source 84 through an irrigation lumen 86. Each irrigation lumen 86 may include a first portion 86A that extends through the distal tip electrode 34 and a second portion 86B that extends through the elongate body 22, and the first portion 86A and the second portion 86B may be in fluid communication with each other when the device is assembled, and fluidly isolated from other parts of the device 12, such that the first 86A and second 86B portions of each irrigation lumen 86 are joined to form a continuous irrigation lumen 86 extending from the irrigation aperture 82 to the fluid source 84. However, in one embodiment, a single irrigation lumen 86 may be directly coupled to the fluid source 84 and may branch downstream of the fluid source 84 into a plurality of irrigation lumens 86. The irrigation aperture(s) 82 may be used to deliver a fluid to the distal tip electrode 34 and environment external to the distal tip electrode 34, such as to cool the distal tip electrode 34 and/or a tissue treatment site during an ablation procedure. In a non-limiting example, the fluid source may contain a biocompatible fluid such as saline with normal, hypotonic, or hypertonic NaCl concentrations. In another non-limiting example, the fluid source may provide genetic materials that are intended to be transfected into tissues through electroporative processes following pulsed energy deliveries. In another non-limiting example, the fluid source may provide nitrates to counteract blood vessel spasms that might otherwise occur. In another non-limiting example, the fluid source may contain adjuvants such as calcium to enhance cell death from electroporation energy deliveries.

Referring again to FIG. 1, the medical device 12 may include a handle 90 coupled to the elongate body proximal portion 26. The handle 90 may include circuitry for identification and/or use in controlling of the medical device 12 or another component of the system 10. Additionally, the handle 90 may also include connectors that are mateable to the control unit 14 to establish communication between the medical device 12 and one or more components or portions of the control unit 14. The handle 90 may also include one or more actuation or control features that allow a user to control, deflect, steer, or otherwise manipulate a distal portion of the medical device 12 from the proximal portion of the medical device 12. For example, the handle 90 may include one or more components such as a lever or knob for manipulating the elongate body 22 and/or additional components of the medical device 12.

Although not shown, the system 10 may include one or more sensors to monitor the operating parameters throughout the system, including for example, pressure, temperature, flow rates, volume, power delivery, impedance, or the like in the control unit 14 and/or the medical device 12, in addition to monitoring, recording or otherwise conveying measurements or conditions within the medical device 12 or the ambient environment at the distal portion of the medical device 12. The sensor(s) may be in communication with the control unit 14 for initiating or triggering one or more alerts or therapeutic delivery modifications during operation of the medical device 12. One or more valves, controllers, or the like may be in communication with the sensor(s) to provide for the controlled dispersion or circulation of fluid through the lumens/fluid paths of the medical device 12. Such valves, controllers, or the like may be located in a portion of the medical device 12 and/or in the control unit 14.

As used herein, the term "control unit 14" for simplicity may include any system components that are not part of the medical device 12 itself, other than components of the navigation system 16 and the imaging system (if included), regardless of whether the component is physically located within or external to the control unit 14. Further, the navigation system 16 may be a standalone system in communication with the control unit 14 or may be contained within or integrated with the control unit 14, even though it is shown as being physically separated from the control unit in FIG. 1. The control unit 14 may include one or more components for the delivery of one or more energy modalities for which the system is used, including therapeutic waveform generators, or laser energy. For example, the control 14 unit may include an energy source 46 as a treatment or diagnostic mechanism in communication with the treatment element(s) of the device 12. As a non-limiting example, the energy source 46 may be an RF generator having a plurality of output channels and operable in one or more modes of operation (for example, unipolar mode and/or bipolar mode) and or may be configured to deliver electrical energy, such as high-voltage energy. In some embodiments, the control unit 14 also includes a laser energy source 48 for delivering laser energy to target tissue through one or more optical windows 38. The control unit 14 may also include a light emitter 44 and light receiver 45 that are in optical communication with and configured to transmit and receive, respectively, light through the optical fiber(s) 62. In one embodiment, the light energy is high-intensity laser light to enable greater penetration into the target tissue.

The control unit 14 may further include processing circuitry 92 that may include one or more controllers, processors, light sources, spectrometers, polarizers, optical filters, multiplexers, and/or software modules configured to execute instructions or algorithms to provide for the automated operation and performance of the features, sequences, calculations, or procedures described herein and/or required for a given medical procedure. In one embodiment, the processing circuitry may include a processor and a memory. The memory may be in electrical communication with the processor and have instructions that, when executed by the processor, configure the processor to receive, process, or otherwise use signals from the device 12. Further, the control unit 14 may include one or more user input devices, controllers, and displays 94 for collecting and conveying information from and to the user. In one embodiment, the system (for example, the control unit 14) includes a charge coupled device (CCD camera) that receives light transmitted through the optical fiber(s) 62 and creates a digital image of the interrogated tissue. In one embodiment, the CCD camera is, or includes, the light receiver 45.

Figure 5:
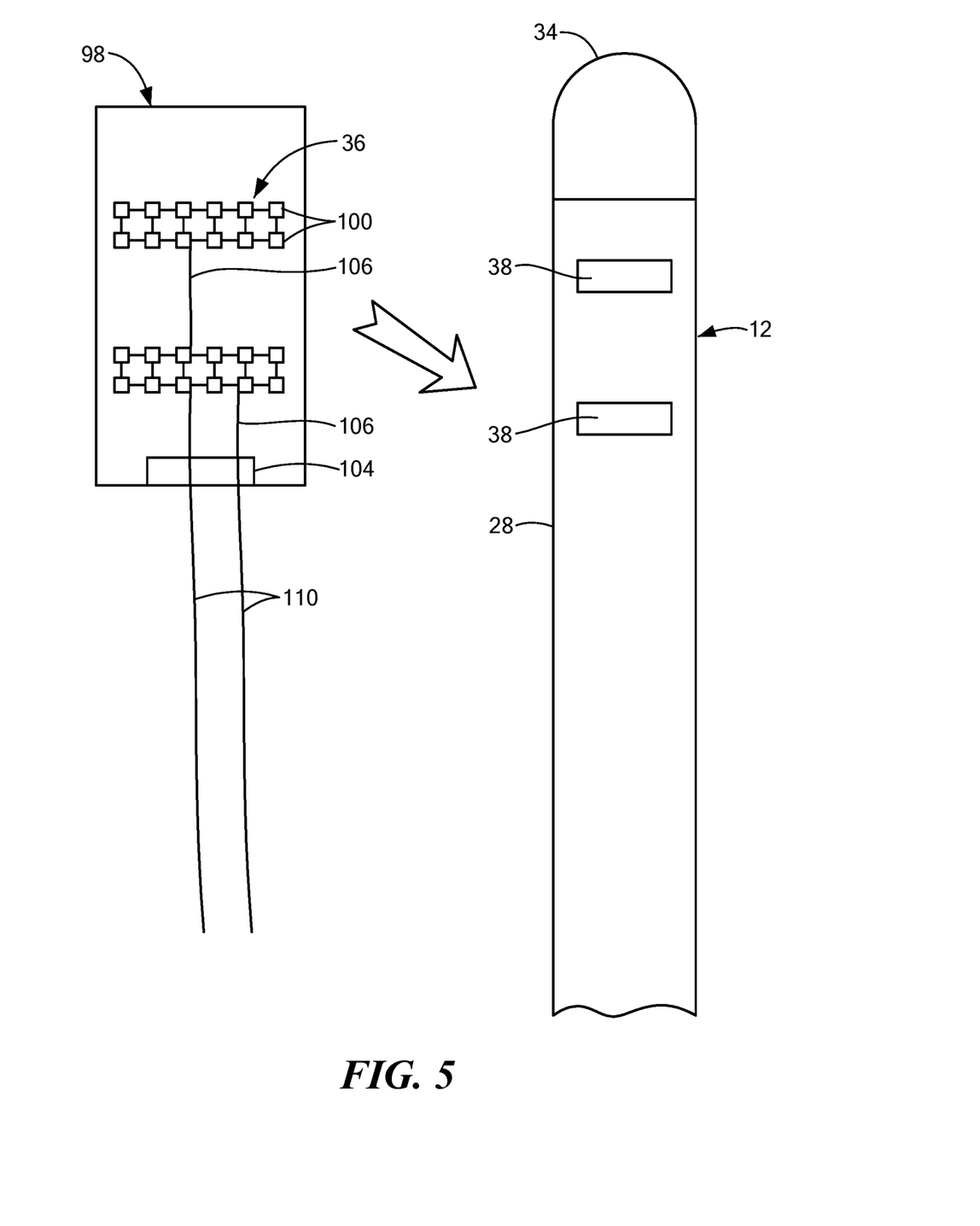
FIG. 5 shows a first exemplary flexible overlay for a medical device having a first configuration of optical windows.
Figure 6:
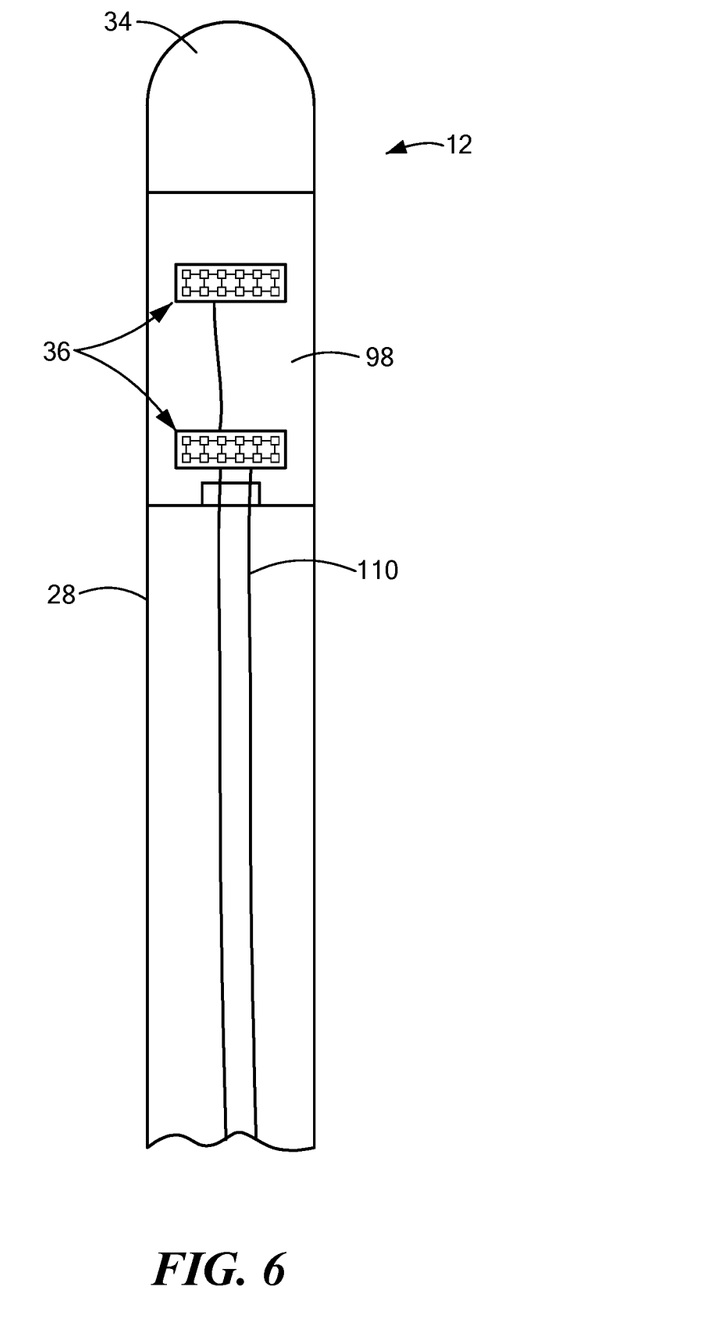
FIG. 6 shows the assembled medical device and flexible overlay of FIG. 5.
Figure 7:
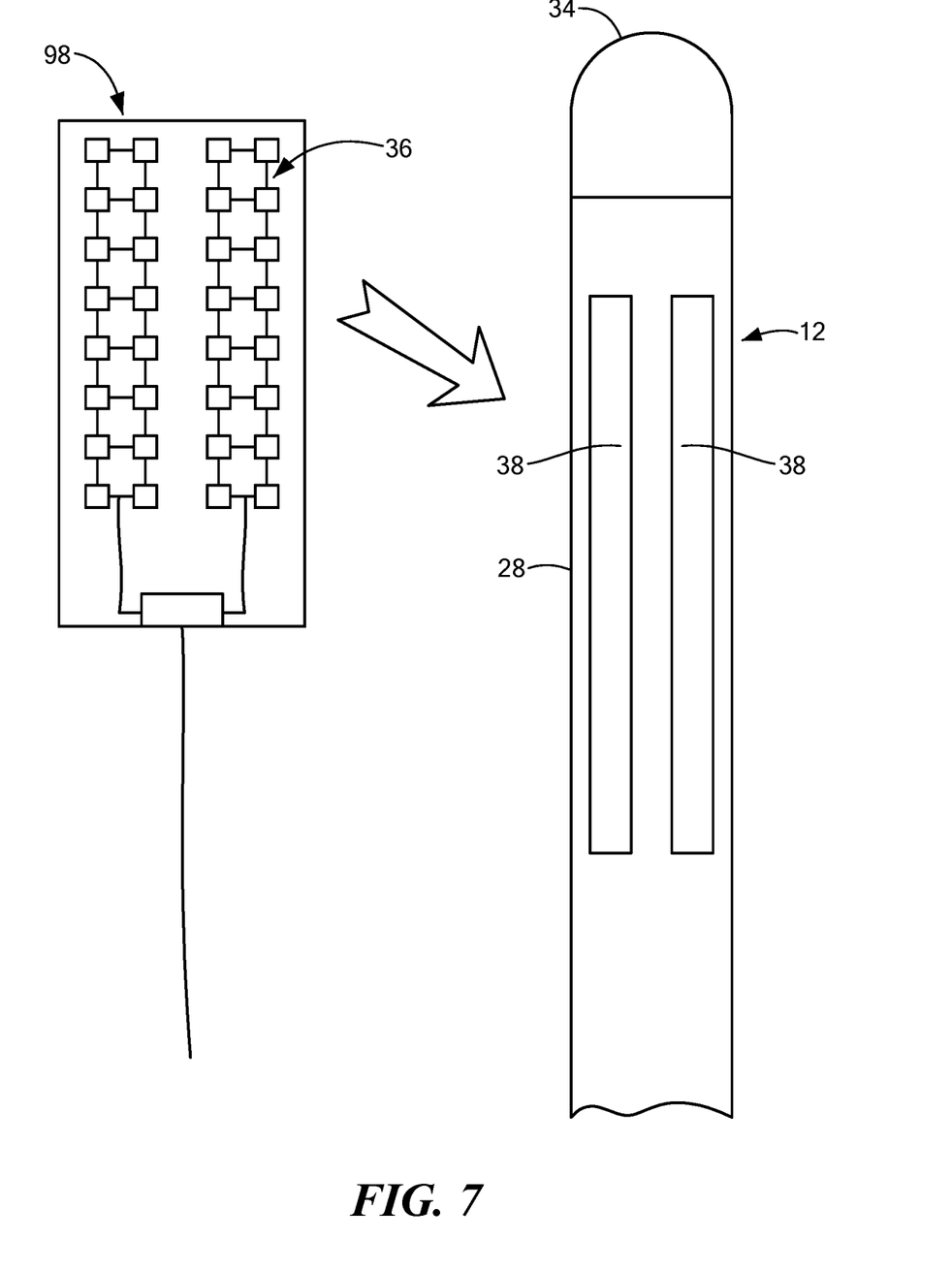
FIG. 7 shows a second exemplary flexible overlay for a medical device having a second configuration of optical windows.
Figure 8:
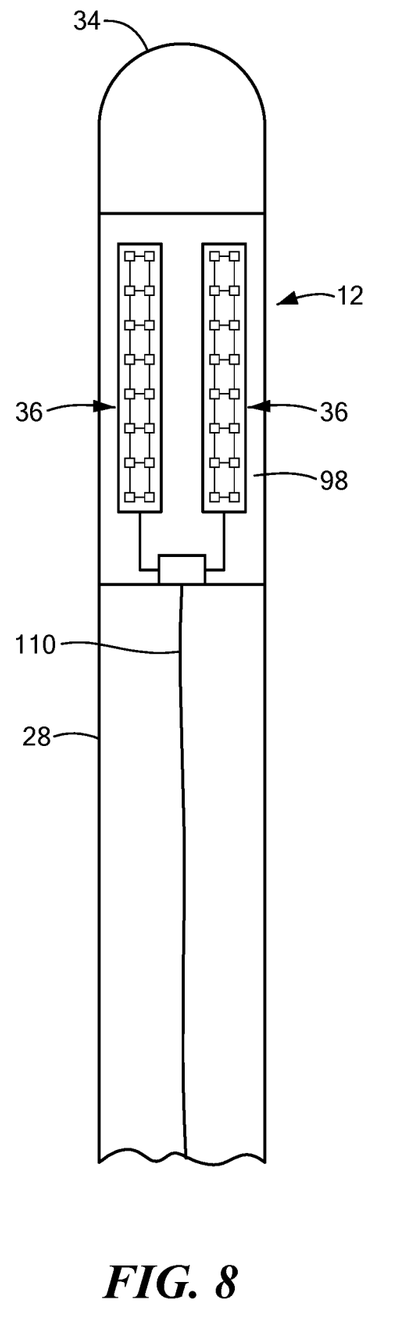
FIG. 8 shows the assembled medical device and flexible overlay of FIG. 7.

Referring now to FIGS. 5-11, the distal portion of an exemplary medical device 12 is now described in more detail. As noted above, the device 12 may include one or more treatment elements, such as a distal tip electrode 34 and, optionally, one or more electrically and/or thermally conductive areas on a location of the elongate body 22 other than at the distalmost tip of the elongate body distal portion 28. As noted above, these electrically and/or thermally conductive areas may be referred to herein for simplicity as lateral electrodes 36. The lateral electrodes 36 are shown in FIG. 1 as being configured like band electrodes; however, the lateral electrodes 36 may have any suitable shape and/or configuration, and non-limiting examples of their manufacture are described in more detail below. The distal tip electrode 34 may be configured and coupled to the elongate body 22 as shown and described in FIGS. 1-4. The elongate body distal portion 28 may include one or more optical windows 38 in the lateral walls of the elongate body 22 (that is, along a length of the elongate body 22 rather than at the distalmost end face). The optical window(s) 38 may each be an area of optically transparent material that is set into, integrated with, or otherwise incorporated into the elongate body distal portion 28. In one embodiment, the elongate body 22 is composed of an opaque, flexible, biocompatible material (for example, polyether ether ketone (PEEK) or similar), whereas each optical window 38 is composed of a transparent biocompatible material (such as transparent ceramic, sapphire, or the like) that is inset or incorporated into an aperture within the elongate body 22 (as shown in FIGS. 5 and 6).

The lateral electrode(s) 36 may be printed, deposited, or affixed onto, or otherwise incorporated onto or into, a flexible overlay 98 that can be applied, affixed, adhered, or otherwise attached to an outer surface of the elongate body 22. Further, the device 12 may include more than one flexible overlay 98. In one embodiment, the flexible overlay 98 is applied to the elongate body distal portion 28, with at least a portion of the flexible overlay 98 being located on an outer surface of at least one optical window 38. The flexible overlay 98 may be composed of one or more layers of transparent, flexible, and biocompatible material(s), such as polyimide. The flexible overlay 98 is shown in FIG. 5 as having a rectangular shape for ease of illustration; however, it will be understood that the flexible overlay 98 may have any suitable shape or configuration. For example, the flexible overlay 98 may have a serpentine, linear, helical, polygonal, or other shape. Further, the flexible overlay 98 may be sized and configured to at least partially encircle a circumference of the elongate body distal portion 28. In one embodiment, the flexible overlay 98 has a helical shape that is configured to be wound around a portion of the elongate body 22 at least once to form one or more bands.

The flexible overlay 98 may include more than one layer of material. In one embodiment, the entirety of the flexible overlay 98 may be transparent. In another embodiment, at least those portions of the flexible overlay 98 that are configured and arranged to be affixed over one or more optical windows 38 in the elongate body 22 may be transparent. In one embodiment, the flexible overlay 98 includes a layer configured to be in contact with the elongate body 22, an outer or encapsulation layer 99, and one or more intermediate layers. The lateral electrode(s) 36 may each include one or more conductive areas 100 of graphene, conductive diamond, or other thermally and electrically conductive and optically transparent material. In one embodiment, the conductive areas may be composed of graphene, as this material may be applied in so thin a layer that it does not change the mechanical properties of the substrate (here, the elongate body 22). Further, graphene may have unlimited fatigue by itself and may serve as an electromagnetic interference (EMI) barrier coating while still allowing for the transmission of light.

Figure 9:
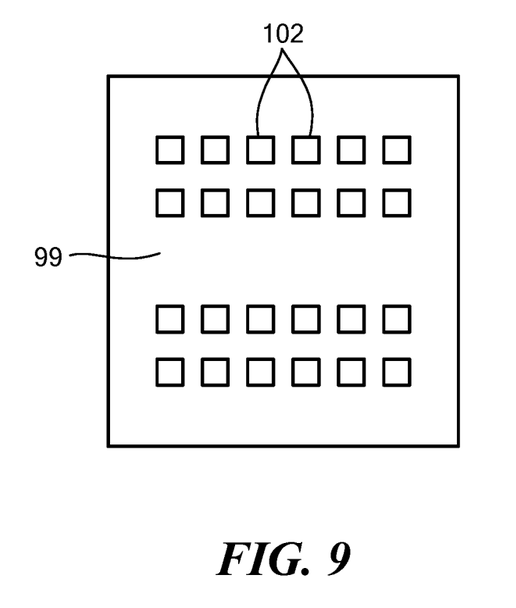
FIG. 9 shows an exemplary encapsulation layer of a flexible overlay having a plurality of holes.

The encapsulation layer 99 may include one or more holes 102, each of which corresponding to a conductive area 100 when the flexible overlay 98 is assembled. A non-limiting example of an encapsulation layer 99 having a plurality of holes 102 is shown in FIG. 9, and these holes 102 may correspond to the conductive areas shown in FIGS. 5 and 6. Each conductive area 100 may be of any suitable size and configuration, but in one non-limiting example, each may be approximately 300 μm². Further, each optical window 38 may have a diameter of between approximately 100 μm and approximately 1000 μm, or have any other appropriate size for collecting adequate amounts of light energy, such that a plurality of conductive areas 100 may be aligned with each optical window 38. The conductive areas 100 associated with each hole 102 in the encapsulation layer 99 may be in contact with a conductive contact pad 104 (for example, the contact pad may be composed of gold, copper, or other electrically conductive material), either directly or via a conductive pathway. For example, graphene or other transparent conductive material may be deposited on a layer of the flexible overlay 98 to form the conductive areas 100 that will correspond to the encapsulation layer holes 102. Further, graphene or other conductive material (which may or may not be transparent) may be deposited on the same layer of the flexible overlay 98 as the conductive areas 100 in, for example, thin lines between the electrode openings 100 and the conductive contact pad 104 to form conductive pathways or traces 106. The encapsulation layer may then be added on top of the conductive areas 100 and the conductive pathways 106. The encapsulation layer may include one or more holes that each corresponds to a conductive area 100, thus creating the electrode openings 102 when the flexible overlay 98 is assembled. In one embodiment, each lateral electrode 36 may comprise a plurality of conductive areas 100, which may be overlaid on the optical windows 98 when the flexible overlay 98 is affixed to the elongate body 22. The transparent conductive areas 100 may not only allow light transmission through the optical windows 38, but may also be used to deliver RF, pulsed high voltage ablation energy, or other treatment or ablation energy and/or to record optical and/or electrical signals from tissue. Thus, the conductive areas may be used to record signals, and the optical windows 38 may be able to receive light transmission, from the tissue at the precise tissue location(s) to which energy is delivered. The delivery of energy and receipt of light transmission may be conducted simultaneously or in sequence. The encapsulation layer may completely or partially encase, cover, or enclose the conductive pathway(s) 106 and the conductive contact pad(s) 104. One or more wires or traces 110 may be connected to (for example, soldered to) or in electrical communication with each conductive contact pad 104. The wire(s) or trace(s) 110 may run along the outside of the elongate body 22 and/or transverse or pass into the elongate body 22. In one embodiment, the wire(s) 100 may be deposited trace(s) composed of a conductive, high-current-carrying material such as copper and coated with a layer of graphene, which may protect the copper from corrosion. Such traces may then serve as ablation energy delivery electrodes as well.

Further, the conductive areas 100 may be arranged to create any desired lateral electrode 36 pattern. In the non-limiting example shown in FIGS. 5 and 6, the conductive areas 100 may be arranged around at least a portion of a circumference of the elongate body 22 to provide lateral electrodes 36 that are at least substantially similar to band electrodes. In the non-limiting example shown in FIGS. 7 and 8, the conductive areas 100 may be arranged in one or more linear patterns that are each configured to extend along the elongate body 22 and be at least substantially parallel to the elongate body longitudinal axis 30.

In an alternative configuration of the device 12, the conductive areas 100 and any connecting wire(s) or trace(s) 106, 110 may be applied directly to the elongate body 22, and in particular over the optical window(s) 38, to provide the ability to deliver treatment energy to tissue and/or record signals from tissue without the need to create and apply a flexible overlay 98.

If the device 12 is used to deliver only laser energy from the optical windows 38, the device 12 may not include a flexible overlay 98 with conductive areas 100. Instead, laser energy may be delivered to tissue at a target treatment location through the optical windows 38 without the need for conductive areas 100. Alternatively, the device 12 may include a flexible overlay 98 affixed to the elongate body 22 such that one or more conductive areas 100 are over one or more optical windows 38. In this configuration, laser energy may be delivered through the optical windows 38 and the conductive areas 100 may be used to record signals from tissue such as intracardiac electrograms. Thus, the conductive areas 100 may be used to record signals from the tissue at the precise tissue location(s) to which laser energy is delivered. Additionally or alternatively, the delivery of energy and receipt of light transmission may be conducted simultaneously or in sequence. For example, laser energy may be pulsed and tissue interrogation light may be delivered between laser energy deliveries. The tissue interrogation light may evoke the fluorescence and/or reflectance response to be measured, and this, in turn, may allow the system 10 and/or the user to monitor the progress of the laser ablation procedure. The laser pulse deliveries could then be halted when an end-point or other indication of sufficient ablation is detected. Further, this technique may also be used for RF or pulsed electric field ablation by irreversible electroporation.

Figure 10:
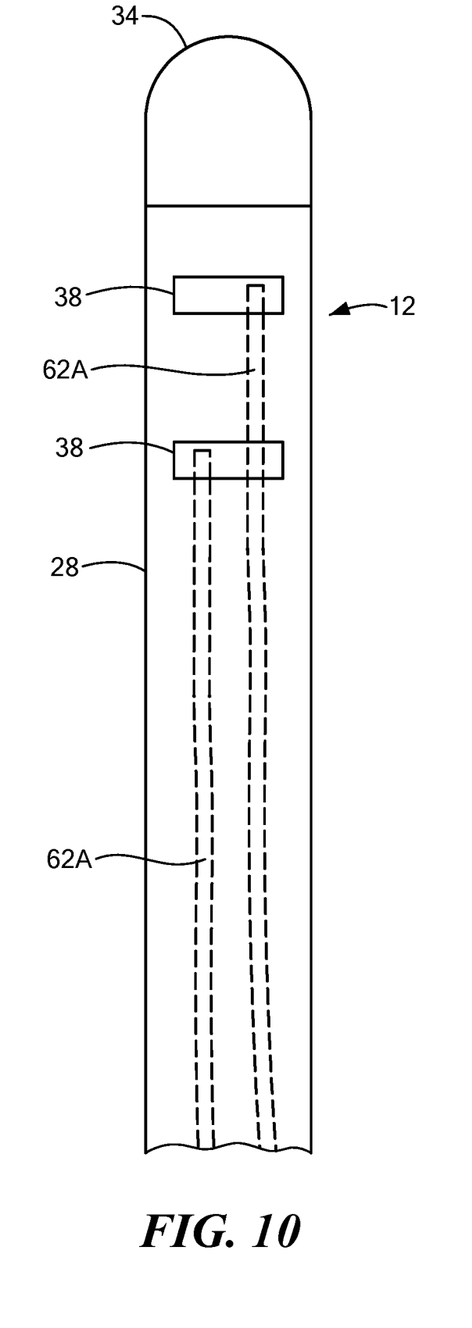
FIG. 10 shows an exemplary medical device having optical windows and an optical distal tip electrode.

As shown in FIG. 10, the device may further include one or more optical fibers 62A in optical communication with the optical windows 38 in the elongate body 22. These optical fibers are indicated with reference number 62A in FIG. 10 for illustration, but all optical fibers may be referred to herein with reference number 62 for simplicity. In the non-limiting example shown in FIG. 10, the elongate body 22 may include a plurality of optical windows 38 and, optionally, a plurality of lateral electrodes 36. The optical fibers 62 that are in optical communication with the optical windows 38 may enable tissue sensing from lateral surface of the device. This may allow the light receiver 45 to receive light energy from a larger area of tissue than when the distal tip electrode 34 is used, and may also allow for the collection of light energy through not only the distal tip of the device 12, but also along the length of the elongate body 22.

Each lateral electrode 36 may be in electrical communication with the control unit 14 and may be used to deliver energy from the energy source 46 to an area of tissue and/or to record electrical signals from the area of tissue. Additionally or alternatively, laser energy from the laser energy source 48, for example, emitting 790 nm light, may be delivered to an area of tissue through the optical window(s) 38 in the elongate body 22. For example, electrical, RF, pulsed RF, electroporation, and/or laser energy may be delivered by the device 12 to treat or ablate an area of tissue. The distal tip electrode 34 and/or lateral electrode(s) 36 may be positioned so that they are in contact with or proximate an area of tissue and can deliver light and/or energy to the tissue and receive signals (for example, optical signals) from the tissue.

In addition to ablating or treating tissue with energy, the device 12 may be used to perform optical sensing of an area of tissue to identify a chemistry or chemical state of the tissue and/or to identify the tissue structure. This data may indicate to the user whether the area of tissue has been sufficiently ablated. In some embodiments of the device 12, each optical fiber 62 may have a distal portion 78 that is at least partially located within or otherwise connected to the distal tip electrode 34 (as shown and described in FIG. 2) and a proximal end (not shown) that is in optical communication with the light emitter 44. Light may be transmitted through each optical fiber 62 from the light source 44 and out of the distal tip electrode 34. The light may then be reflected back into the optical fiber 62 and transmitted back to the light receiver 45. The light receiver 45 may convert this light energy into an electrical signal, which it may then transmit to the control unit processing circuitry 92. In one embodiment that delivers pulsed 790 nm laser energy to ablate tissue, a diagnostic signal could be sent prior to delivering the ablative laser light to ensure that the ablation window was directed into targeted tissue and not directed into open blood or a layer of blood that might otherwise be carbonized when laser light is delivered.

In one embodiment, the optical fiber(s) 62 may be used to detect fluorescence that is naturally emitted by the reduced form of nicotinamide adenine dinucleotide (NADH) and/or nicotinamide adenine dinucleotide phosphate (NADPH), both of which being coenzymes that are involved in cellular metabolism and the transfer of electrons from one reaction to another. For example, it has been found that mitochondrial NADH emits blue fluorescence when illuminated with ultraviolet light. However, when tissue is ablated, this fluorescence is greatly reduced or eliminated. Thus, the optical fiber(s) 62 will receive little or no fluorescence from ablated tissue when that tissue is interrogated with ultraviolet light (that is, when ultraviolet light is delivered from the light emitter 44 through the optical fiber(s) 62 to the tissue). For example, NADH absorbs light at a wavelength of approximately 340 nm (±30 nm) and emits fluorescence at a wavelength of approximately 460 nm (±50 nm). Ultraviolet light is electromagnetic radiation with a wavelength of between approximately 10 nm and 400 nm; however, it will be understood that other wavelengths may be emitted by the light emitter 44, reflected or fluoresced from the tissue, and/or received by the light receiver 45.

In an additional or alternative embodiment, the optical fiber(s) 62 may be used to identify the type of tissue or tissue structure being interrogated by the device 12. Different tissues have different optical properties that may be detected by the device 12. For example, fatty tissue, pulmonary vein tissue, the fossa ovalis, cardiac muscle, and blood all have difference reflectance values that can be used by the system 10 to identify a type of tissue with which the electrode(s) 34, 36 are in contact.

Figure 11:
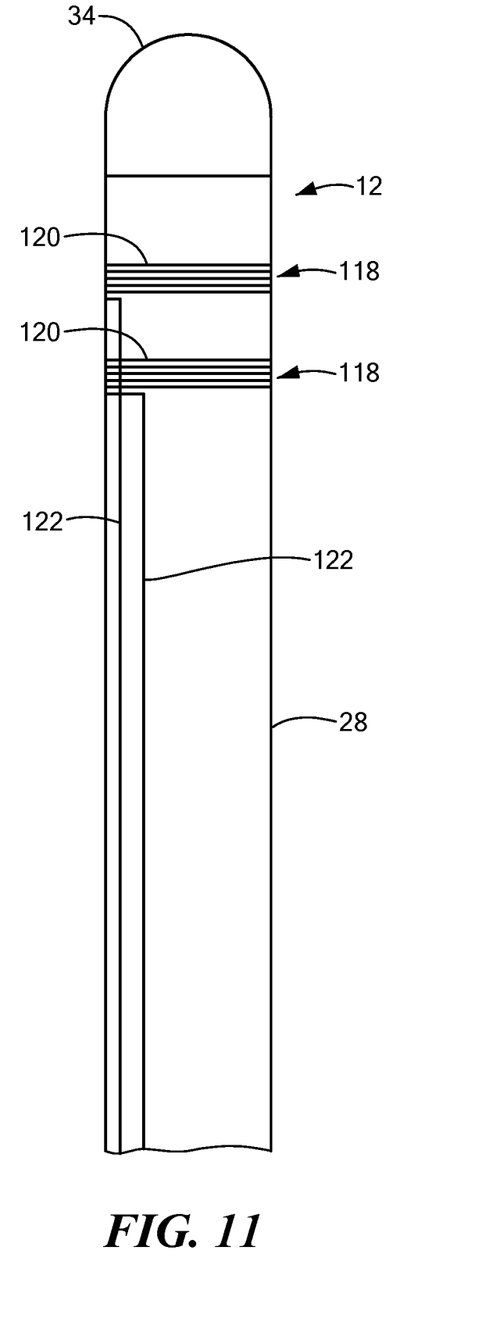
FIG. 11 shows an exemplary medical device having an optical distal tip electrode and non-optical lateral electrodes.

Referring now to FIG. 11, an exemplary medical device is shown that includes an optical distal tip electrode 34 and one or more lateral electrodes without optical window(s) 38 or other transparencies. These electrodes may be referred to herein as non-optical lateral electrodes 118. The device 12 shown in FIG. 11 may be used to collect light energy or other optical signals from tissue through the distal tip electrode 34, whereas the distal tip electrode 34 and the non-optical lateral electrodes 118 may both be used to deliver treatment or ablation energy to the tissue. The non-optical lateral electrodes 118 may be wires that are wound at least once around a portion of the elongate body distal portion 28 (as shown in FIG. 11). For example, each non-optical electrode 118 may be composed of a single piece or strand of conductive material, such as copper, tantalum, or gold, that has an electrode portion 120 that is wrapped around a circumference of the elongate body distal portion 28 at least once (for example, to form a band-electrode-like conductive region) and a wire portion 122 that extends from the electrode portion 120 proximally to the handle 90. The electrode portion 120 may be electrically and thermally conductive, whereas the wire portion 122 may have an electrically and thermally insulative coating. Additionally or alternatively, the non-optical lateral electrodes 118 may be band electrodes and may be connected to an electrode wire. However, it will be understood that the non-optical lateral electrodes 118 may have any suitable size, configuration, or shape.

In an exemplary method of use, the device 12 may be navigated through the patient's vasculature to a target treatment location within the patient's heart. Once the device 12 is located proximate the target treatment location, light may be emitted from the light emitter 44 through one or more optical fibers 62 toward tissue at the target treatment location ("interrogated tissue"). For example, light may be emitted through the optical fibers 62 that are in optical communication with the distal tip electrode 34 and one or more optical windows 38. That light may then be reflected from the interrogated tissue through the distal tip electrode 34 and/or the optical window(s) 38, transmitted back through the optical fiber(s) 62, received by the light receiver 45, converted to electrical signals, and then transmitted to the control unit processing circuitry 92. Based on the reflectance values from the interrogated tissue, the processing circuitry 92 may determine whether the device 12 is in a correct position to treat the tissue target tissue location. For example, reflectance values may be used to determine whether the device is in contact with atrial wall tissue, pulmonary vein tissue, or is not in contact with tissue and is instead surrounded by blood. Additionally, the optical fiber(s) 62 may be used to detect fluorescence from the tissue at the target treatment location to establish a pre-treatment or baseline fluorescence value.

Once it is determined that the device 12 is in the correct position, energy may be delivered from the device to treat or ablate tissue at the target treatment location. For example, RF energy may be delivered by the distal tip electrode 34, RF energy may be delivered by one or more lateral electrodes 36, and/or laser energy may be delivered through the optical window(s) 38. During and/or after the delivery of treatment or ablation energy, the optical fiber(s) 62 may be used to detect fluorescence form the tissue at the target treatment location, and the processing circuitry 92 may compare this in-treatment and/or post-treatment fluorescence to the pre-treatment or baseline fluorescence. The comparison may indicate whether the tissue has been sufficiently ablated. If the tissue has been sufficiently ablated, the user may end the treatment procedure. Otherwise, this method may be repeated until optical characteristics of the tissue indicate that sufficient ablation has occurred. The comparison may also be used to determine an extent of lesion formation. For example, a plurality of comparisons in a plurality of locations may be made between the pre-treatment or threshold fluorescence and in-treatment and/or post-treatment fluorescence to identify a boundary of an area sufficiently ablated tissue and, therefore, to identify the size of the lesion. Further, the distal tip electrode 34 and/or the conductive material of the lateral electrodes 36 may be used to record electrical signals from the tissue, including intracardiac electrograms. These signals may be used by the processing circuitry 92 to determine if such signals are of local origin or produced from far field depolarizations.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A device for performing a medical procedure, the device comprising:
   an elongate body including a proximal portion, a distal portion having a distal end, and a longitudinal axis;
   a distal tip electrode at the distal end;
   at least one optical window within the distal portion of the elongate body, the at least one optical window being proximal to the distal tip electrode;
   at least one lateral electrode disposed along a length of the elongate body distal portion having a plurality of electrically conductive and optically transparent areas; and
   at least one flexible overlay configured to extend partially around a portion of the elongate body, the at least one flexible overlay having a plurality of layers, the plurality of layers including an inner layer configured to be in contact with the elongate body, an encapsulation layer, and at least one intermediate layer disposed between the inner layer and the encapsulation layer, the encapsulation layer having a plurality of openings corresponding to each of the plurality of electrically conductive and optically transparent areas.

2. The device of claim 1, wherein the distal tip electrode is optically transparent and electrically conductive.

3. The device of claim 1, wherein the distal tip electrode is optically transparent thermally conductive.

4. The device of claim 1, wherein the distal tip electrode includes a proximal face and a curved distal surface, the proximal face lying in a plane that is orthogonal to the longitudinal axis of the elongate body.

5. The device of claim 4, further comprising at least one optical fiber within the elongate body, the at least one optical fiber being in optical communication with the distal tip electrode.

6. The device of claim 5, wherein the distal tip electrode further includes an optical fiber channel having an opening, the optical fiber opening being on the proximal face of the distal tip electrode.

7. The device of claim 6, wherein the optical fiber channel extends within the distal tip electrode from the proximal face of the distal tip electrode to a location that is a distance from the curved distal surface of the distal tip electrode.

8. The device of claim 7, wherein the optical fiber channel is sized and configured to accept at least a portion of the at least one optical fiber.

9. The device of claim 8, wherein the at least one optical fiber is a first at least one optical fiber, the device further comprising a second at least one optical fiber, each of the second at least one optical fiber being in optical communication with one of the at least one optical window.

10. The device of claim 1, wherein the at least one optical window is composed of an optically transparent material.

11. The device of claim 1, wherein the at least one flexible overlay is applied to the distal portion of the elongate body.

12. The device of claim 11, wherein the flexible overlay is at least partially composed of an optically transparent material such that the flexible overlay is optically transparent, the at least one flexible overlay being applied to the elongate body such that at least some of the plurality of electrically conductive and optically transparent areas are positioned over at least one of the at least one optical window.

13. The device of claim 12, wherein the at least one lateral electrode is wound around at least a portion of the elongate body.

14. The device of claim 1, wherein the distal tip electrode includes a plurality of apertures, the plurality of apertures configured to be in fluid communication with a fluid source.

15. A system for evaluating and treating an area of tissue, the system comprising:
a medical device including:
an elongate body including a proximal portion, a distal portion having a distal end, and a longitudinal axis;
a distal tip electrode disposed at the distal end;
a first plurality of optical fibers within the elongate body and in optical communication with the distal tip electrode;
at least one optical window within the distal portion of the elongate body, the at least one optical window being composed of an optically transparent material;
a second plurality of optical fibers within the elongate body and in optical communication with the at least one optical window;
at least one lateral electrode on the distal portion of the elongate body, the at least one lateral electrode being a plurality of electrically conductive and optically transparent areas, the plurality of electrically conductive and optically transparent areas being aligned with the at least one optical window such that the plurality of electrically conductive and optically transparent graphene areas and the at least one optical window are configured to transmit light therethrough;
a flexible overlay applied to at least a portion of the distal portion of the elongate body, the flexible overlay having a plurality of layers, the plurality of layers including an inner layer configured to be in contact with the elongate body, an encapsulation layer, and at least one intermediate layer disposed between the inner layer and the encapsulation layer, the encapsulation layer having a plurality of openings corresponding to each of the plurality of electrically conductive and optically transparent areas; and
a control unit including:
a light emitter in optical communication with each of the first plurality of optical fibers and the second plurality of optical fibers;
a light receiver in optical communication with each of the first plurality of optical fibers and the second plurality of optical fibers; and
an energy source in communication with the distal tip electrode and the at least one lateral electrode; and
a processing circuitry in communication with the first plurality of optical fibers, the second plurality of optical fibers, the distal tip electrode, and the at least one lateral electrode.

16. The system of claim 15, wherein the system is configured to deliver treatment energy from the at least one lateral electrode to the area of tissue.

17. The system of claim 16, wherein the system is further configured to emit and receive light through the at least one lateral electrode and the at least one optical window to and from the area of tissue.

18. The system of claim 17, wherein the processing circuitry is configured to:
emit light from the light emitter through at least one of the distal tip electrode and the at least one lateral electrode through at least one of the first plurality of optical fibers and the second plurality of optical fibers to the area of tissue;
receive light fluoresced from the area of tissue through at least one of the distal tip electrode and the at least one lateral electrode through at least one of the first plurality of optical fibers and the second plurality of optical fibers; and
determine whether the area of tissue has been treated based on the received light.

19. A system for evaluating and ablating an area of tissue, the system comprising:
a medical device including:
an elongate body including a proximal portion, a distal portion having a distal end, and a longitudinal axis;
a distal tip electrode at the distal end of the elongate body, the distal tip electrode being optically transparent and electrically conductive;
a first plurality of optical fibers within the elongate body and in optical communication with the distal tip electrode;
a plurality of optical windows within the distal portion of the elongate body, at least one optical window from the plurality of optical windows being composed of an optically transparent material;
a second plurality of optical fibers within the elongate body, each of the second plurality of optical fibers being in optical communication with at least one of the plurality of optical windows;
a flexible overlay applied to at least a portion of the distal portion of the elongate body, the flexible overlay having:
at least one layer composed of a flexible and optically transparent material, the at least one layer including an inner layer configured to be in contact with the elongate body, an encapsulation layer, and at least one intermediate layer disposed between the inner layer and the encapsulation layer;
a plurality of electrically conductive and optically transparent graphene areas on the at least one layer, the plurality of electrically conductive and optically transparent graphene areas being aligned with at least one of the plurality of optical windows; and
the encapsulation layer having a plurality of openings corresponding to each of the plurality of electrically conductive and optically transparent graphene areas;
a control unit including:
a light emitter in optical communication with each of the first plurality of optical fibers and the second plurality of optical fibers;
a light receiver in optical communication with each of the first plurality of optical fibers and the second plurality of optical fibers;

an energy source in communication with the distal tip electrode; and a processing circuitry in communication with the first plurality of optical fibers, the second plurality of optical fibers, the distal tip electrode, the processing circuitry being programmed to:

deliver energy to the area of tissue through at least one of the distal tip electrode and the plurality of electrically conductive and optically transparent areas;

emit light from the light emitter through at least one of the distal tip electrode and at least one lateral electrode through at least one of the first plurality of optical fibers and the second plurality of optical fibers to the area of tissue;

receive light that is at least one of fluoresced and reflected from the area of tissue through at least one of the distal tip electrode and the at least one lateral electrode through at least one of the first plurality of optical fibers and the second plurality of optical fibers; and determine whether the area of tissue has been ablated based on the received light.

20. The system of claim 19, wherein the light emitted is a laser emitter.

\* \* \* \* \*